US007053043B1

(12) United States Patent
Aharoni et al.

(10) Patent No.: US 7,053,043 B1
(45) Date of Patent: May 30, 2006

(54) PHARMACEUTICAL COMPOSITIONS COMPRISING SYNTHETIC PEPTIDE COPOLYMERS AND METHODS FOR PREVENTING AND TREATING GVHD AND HVGD

(75) Inventors: Rina Aharoni, Rehovot (IL); Dvora Teitelbaum, Rehovot (IL); Ruth Arnon, Rehovot (IL)

(73) Assignee: Yeda Research and Development Co.Ltd., Rehovot (IL)

( * ) Notice: Subject to any disclaimer, the term of this patent is extended or adjusted under 35 U.S.C. 154(b) by 0 days.

(21) Appl. No.: 09/831,629

(22) PCT Filed: Nov. 12, 1999

(86) PCT No.: PCT/US99/27107

§ 371 (c)(1),
(2), (4) Date: Aug. 17, 2001

(87) PCT Pub. No.: WO00/27417

PCT Pub. Date: May 18, 2000

Related U.S. Application Data

(60) Provisional application No. 60/145,219, filed on Jul. 23, 1999.

(51) Int. Cl.
*A61K 38/02* (2006.01)
(52) U.S. Cl. .............................. 514/2; 514/12; 514/13; 514/14; 530/324; 530/325; 530/326
(58) Field of Classification Search .................... 514/2, 514/12–14; 530/324, 325, 326
See application file for complete search history.

(56) References Cited

U.S. PATENT DOCUMENTS

| 4,339,431 | A | | 7/1982 | Gaffar |
| 5,182,262 | A | * | 1/1993 | Leto .............................. 514/13 |
| 5,204,099 | A | | 4/1993 | Barbier et al. |
| 5,500,412 | A | * | 3/1996 | Carney et al. ................ 514/13 |
| 5,858,964 | A | | 1/1999 | Aharoni et al. |
| 5,958,882 | A | * | 9/1999 | Jameson et al. .............. 514/13 |
| 5,962,634 | A | * | 10/1999 | Jameson et al. ............. 530/324 |
| 6,046,289 | A | * | 4/2000 | Komazawa et al. ..... 526/238.1 |
| 6,075,004 | A | * | 6/2000 | Benedict et al. ................ 514/2 |
| 6,180,600 | B1 | * | 1/2001 | Jameson et al. ................ 514/9 |
| 6,436,903 | B1 | * | 8/2002 | Clayberger et al. ........... 514/15 |
| 6,844,421 | B1 | * | 1/2005 | Korngold et al. ........... 530/328 |

FOREIGN PATENT DOCUMENTS

| WO | WO 92/02543 A1 | 2/1992 |
| WO | WO 94/26774 A1 | 11/1994 |
| WO | WO 95/26980 A2 | 10/1995 |
| WO | WO 95/31997 A1 | 11/1995 |
| WO | WO 96/32119 A1 | 10/1996 |

OTHER PUBLICATIONS

Sigma Catalog, 1991 Edition, pp. 1045-1050.*
Wagner (Introduction to Statistics, pp. 82-140, Harper Collins Publishers, 1992).*
Aharoni, Transplantation 72, 598-605, 2001.*
Aharoni et al, "Studies on the mechanism and specificity of the effect of the synthetic random coploymer GLAT on graft-versus-host disease", *Immunol Lett* 58(2):79-87 (1997).
Fridkis-Hareli et al, "Direct binding of myelin basic protein and synthetic copolymer 1 to class II major histocompatibility complex molecules on living antigen-presenting cells—specificity and promiscuity", *Proc Natl Acad Sci USA* 91(11):4872-4876 (1994).
Fridkis-Hareli et al, "Binding of random copolymers of three amino acids to class II MHC molecules", *Int. Immunol* 11(5):635-641 (1999).
Li et al, "Glatiramer acetate blocks the activation of THP-1 cells by interferon-gamma", *Eur J Pharmacol* 342(2-3):303-310 (1998).
Schlegel et al, "A synthetic random basic copolymer with promicuous binding to class II major histocompatibility complex molecules inhibits T-cell proliferative response to major and minor histocompatibility antigens in vitro and confers the capacity to prevent murine graft-versus-host disease in vivo", *Proc Natl Acad Sci USA* 93(10):5061-5066 (1996).
Sela et al, "Suppressive activity of COP-1 in EAE and its relevance to multiple sclerosis", *Bull Inst Pasteur* 88:303-314 (1990).
Teitelbaum et al, "Suppression of experimental allergic encephalomyelitis by a synthetic polypeptide", *Eur J Immunol* 1(4):242-248 (1971).
Teitelbaum et al, "Cross-reaction and specificities of monoclonal antibodies against myelin basic protein and against the synthetic copolymer 1", *Proc Natl Acad Sci USA* 88(21):9528-19532 (1991).
Teitelbaum et al, "Synthetic copolymer 1 inhibits human T-cell lines specific for myelin basic protein", *Proc Natl Acad Sci USA* 89(1):137-141 (1992).
Teitelbaum et al, "Copolymer 1 from the laboratory to FDA", *Isr J Med Sci* 33(4):280-284 (1997).

(Continued)

*Primary Examiner*—David Lukton
(74) *Attorney, Agent, or Firm*—Browdy and Neimark, PLLC

(57) ABSTRACT

Compositions and methods for treating and preventing host-versus-graft disease and graft-versus-host disease comprising as active ingredient random copolymers of amino acids comprising one amino acid from at least three of the following groups: (a) lysine and arginine; (b) glutamic acid and aspartic acid; (c) alanine and glycine; and (d) tyrosine and tryptophan; with the proviso that the random copolymer is not Copolymer 1 or D-Copolymer 1 when the disease being treated is graft-versus-host disease.

18 Claims, No Drawings

OTHER PUBLICATIONS

Aharoni et al, "Copolymer 1 induces T cells of the T helper type 2 the crossreact with myelin basic protein and supperss experimental autoimmune encephalomyelitis", *Proc Natl Acad Sci USA* 94(20):10821-10826 (1997).

Arnon et al, "New insights into the mechanism of action of copolymer 1 in experimental allergic encephalomyelitis and multiple sclerosis", *J Neurol* 243(4 Suppl 1):S8-13 (1996).

Johnson et al, "Copolymer 1 reduces relapse rate and improves disability in relapsing-remitting multiple sclerosis: results of a phase III multicenter, double-blind, placebo-controlled trial", *Neurology* 45:1268-1276 (1995).

Schlegel et al, "Prevention of graft-versus-host disease by peptides binding to class II major histocompatibility complex molecules", *Blood* 84(8):2802-2810 (1994).

Teitelbaum et al, "Development of Copolymer 1 (Copaxone®) as a Specific Drug Against Multiple Sclerosis", in *The Decade of Autoimmunity*, Y. Shoenfeld, ed., Elsevier Science B.V., pp 191-196 (1999).

* cited by examiner

SEQUENCE LISTING

<160> NUMBER OF SEQ ID NOS: 6

<210> SEQ ID NO 1
<211> LENGTH: 13
<212> TYPE: PRT
<213> ORGANISM: Artificial Sequence
<220> FEATURE:
<223> OTHER INFORMATION: Description of Artificial Sequence:
    Synthetically derived MBP Ac1-11[4a] myelin basic protein -continued

```
<400> SEQUENCE: 1

Ala Cys Ala Ser Gln Ala Arg Pro Ser Gln Arg His Gly
 1               5                  10

<210> SEQ ID NO 2
<211> LENGTH: 13
<212> TYPE: PRT
<213> ORGANISM: Artificial Sequence
<220> FEATURE:
<223> OTHER INFORMATION: Description of Artificial Sequence:
      Synthetically derived MBP 35-47 protein

<400> SEQUENCE: 2

Thr Gly Ile Leu Asp Ser Ile Gly Arg Phe Phe Ser Gly
 1               5                  10

<210> SEQ ID NO 3
<211> LENGTH: 14
<212> TYPE: PRT
<213> ORGANISM: Artificial Sequence
<220> FEATURE:
<223> OTHER INFORMATION: Description of Artificial Sequence:
      Synthetically derived KM-core extension peptide

<400> SEQUENCE: 3

Lys Met Lys Met Val His Ala Ala His Ala Lys Met Lys Met
 1               5                  10

<210> SEQ ID NO 4
<211> LENGTH: 13
<212> TYPE: PRT
<213> ORGANISM: Artificial Sequence
<220> FEATURE:
<223> OTHER INFORMATION: Description of Artificial Sequence:
      Synthetically derived MBP 89-101 protein

<400> SEQUENCE: 4

Val His Phe Phe Lys Asn Ile Val Thr Pro Arg Thr Pro
 1               5                  10

<210> SEQ ID NO 5
<211> LENGTH: 21
<212> TYPE: DNA
<213> ORGANISM: Artificial Sequence
<220> FEATURE:
<223> OTHER INFORMATION: Description of Artificial Sequence:
      Synthetically derived PCT amplification region of murine IL-1b
      gene

<400> SEQUENCE: 5
ccaagcttcc ttgtgcaagt a                                       21

<210> SEQ ID NO 6
<211> LENGTH: 21
<212> TYPE: DNA
<213> ORGANISM: Artificial Sequence
<220> FEATURE:
<223> OTHER INFORMATION: Description of Artificial Sequence:
      Synthetically derived PCT amplification region of murine IL-1b
      gene

<400> SEQUENCE: 6
aagcccaaag tccatcagtg g                                       21
```

PHARMACEUTICAL COMPOSITIONS COMPRISING SYNTHETIC PEPTIDE COPOLYMERS AND METHODS FOR PREVENTING AND TREATING GVHD AND HVGD

REFERENCE TO RELATED APPLICATIONS

The present application is the national stage under 35 U.S.C. 371 of international application PCT/US99/27107, filed 12 Nov. 1999, which designated the United States, and which international application was published under PCT Article 21(2) in the English language and claims benefit of 60/145,219 filed Jul. 23, 1999.

FIELD OF THE INVENTION

The present invention provides compositions and methods for prevention and treatment of graft rejection in transplantation of tissues and organs from HLA matched and unmatched allogeneic human donors, as well as xenografts from donors of other species. Transplanted organs include hearts, lungs, kidneys, livers, skin and other organs or tissues transplanted from donor to recipient. The present invention also relates to compositions and methods for preventing or treating graft-versus-host disease in bone marrow transplantation.

BACKGROUND OF THE INVENTION

Transplantation systems such as organ transplantations and bone marrow reconstitution have become important and effective therapies for many life threatening diseases. However, immune rejection is still the major barrier for successful transplantation. This is manifested in functional deterioration and graft rejection in the case of organ transplantation (host-versus-graft disease, or HVGD). Another manifestation of pathological immune reactivity is graft-versus-host disease (GVHD) that occurs in approximately 30% of bone marrow recipients. Up to half of those patients who develop GVHD may succumb to this process. This high morbidity and mortality has led to continuous interest in the possibility of controlling or preventing GVHD.

Clinicopathologically, two forms of GVHD have been recognized. Acute GVHD develops within the first 3 months after bone marrow transplantation and features disorders of skin, liver and gastrointestinal tract. Chronic GVHD is a multiorgan autoimmune-like disease, emerging from 3 months up to 3 years post-transplantation and shares features common to naturally occurring autoimmune disorders, like systemic lupus erythematosus (SLE) and scleroderma.

Current available approaches for prevention of GVHD and HVGD include the use of non-specific immunosuppressive drugs, such as cyclosporine, FK506, methotrexate and/or prednisone. However, these treatments induce severe side effects, including nephrotoxicity, hypertension, hypercholesterolemia, diabetogenic effects, neurotoxicity, hirsutism and gengival hyperplasia. Moreover, the unselective depression of the entire immune system renders patients vulnerable to infections. Despite chronic administration of immunosuppressive agents, transplantations have limited success as a therapeutic approach for long term survival. Given these limitations, traditional immunosuppressive therapies cannot overcome the rejection of HLA unmatched transplants and xenografts. Hence, these traditional therapies do not solve the problem of the acute and growing shortage of human donors.

The pathological process of immune rejection is mediated by T-cells that recognize alloantigens presented on self major histocompatibility complex (MHC) molecules, as non-self. They then proliferate, secrete cytokines, and recruit additional inflammatory and cytotoxic cells (Sykes et al., 1996). In MHC matched bone marrow transplantation, GVHD is caused by the competent donor T cells reacting against minor histocompatibility antigens of the recipient. The donor T cells are sensitized to such alloantigens and then directly, or through secondary signals, attack the host cells. In order to prevent immune rejection, it is therefore essential to inhibit antigen presentation and consequently T-cell activation. It has been demonstrated that small synthetic peptides of 11–14 amino acids with high binding affinity for specific class II MHC molecules, were capable of preventing murine graft-versus-host disease (Schlegel et al., 1994). This approach, however, has been limited by the need for allelic specificity of the inhibitor peptides to the MHC haplotype of the donor/recipient, as well as by the difficulty of achieving sustained tissue levels of such low molecular weight peptides over a prolonged period of time.

A high molecular weight synthetic basic random copolymer consisting of L-Ala, L-Glu, L-Lys and L-Tyr residues in the molar ratio of about 6 parts Ala to 2 parts Glu to 4.5 parts Lys to 1 part Tyr, and having a molecular weight of 15,000–25,000, was first described in U.S. Pat. No. 3,849,550 as an agent for treatment or prevention of experimental allergic encephalomyelitis (EAE), a disease resembling multiple sclerosis (MS) that can be induced in susceptible animals. Batches of this copolymer of average molecular weight 23,000, designated Copolymer 1 or Cop 1, were shown to be highly effective in protecting and suppressing EAE in several animal species (Teitelbaum et al., 1971, 1974a, 1974b).

D-Copolymer 1 or D-Cop 1, in which the four amino acids have the D-configuration, namely a random copolymer containing the D-Ala, D-Glu, D-Lys and D-Tyr residues, has also been described (Webb et al., 1976).

Later, Cop 1 was found to significantly reduce the number of relapses in patients with the exacerbating-remitting form of MS (Bornstein et al., 1990; Sela et al., 1990; Johnson et al., 1994). Copolymer 1, in the form of the acetate salts of synthetic polypeptides containing L-Glu, L-Ala, L-Tyr and L-Lys with an average molar fraction of 0.141, 0.427, 0.095 and 0.338, is the active ingredient of COPAXONE®, a medicament for the treatment of multiple sclerosis.

The mechanism underlying the therapeutic activity of Cop 1 in MS has been extensively studied. Cop 1 was found to be immunologically cross-reactive with myelin basic protein (MBP), the main autoantigen in EAE and MS. Its suppressive effect results from several mechanisms, such as inhibition of the autoreactive pathogenic T-cells on one hand (Teitelbaum et al., 1988), and stimulation of suppressor cells on the other hand (Aharoni et al., 1993). The first step essential for the activation of these specific processes is the binding of Cop 1 to the histocompatibility molecules. Indeed, it has been shown that Cop 1, in two different batches of molecular weight 5,550 and 8,600, and relative molar ratio of L-Ala (4.1–5.8 residues), L-Glu (1.4–1.8 residues), L-Lys (3.2–4.2 residues) and L-Tyr (1 residue), binds very efficiently to a variety of MHC class II molecules of mouse and human origin, and furthermore competes with MBP and its major epitope p84-102 for MHC binding and can even displace such antigens that had already been bound to the MHC molecule (Fridkis-Hareli et al., 1994).

Mixed lymphocyte reaction (MLR) which is used clinically to assess immune rejection between donors and recipients was inhibited by Cop 1 (Schlegel et al., 1996). Cop 1 prevents GVHD in a murine model of lethal GVHD, which mimics MHC matched bone marrow transplantation in human (Schlegel et al., 1996). Thus, post transplantation administration of Cop 1 over a limited time after transplantation significantly reduced the incidence onset and severity of disease, resulting in improved long-term survival. Studies on the effect of Cop 1 on various processes involved in the pathological course of immune rejection showed that Cop 1 inhibited T cell proliferation in response to host cell (Aharoni et al., 1997). Cop 1 treatment completely abolished cytotoxic activity toward grafts, prevented the pro-GVHD IL-2 and IFN-γ cytokine secretion, and induced beneficial Th2 anti-inflammatory response. In view of these cumulative data, Cop 1 is a candidate drug for the prevention of GVHD in humans. See WO 96/32119 and U.S. Pat. No. 5,858,964.

None of the prior art publications describes or suggests that Cop 1 may be used to prevent or to treat HVGD, nor that there are other copolymers useful for preventing or treating GVHD or HVGD.

The nomenclature GLAT copolymer or YEAK copolymer has also been used for Cop 1. Thus, hereinafter in the specification and in the claims, the terms Copolymer 1, Cop 1, L-GLAT and L-YEAK will be used interchangeably for the L form of Cop 1, and the terms D-Copolymer 1, D-Cop 1, D-GLAT and D-YEAK will be used interchangeably for the D form of Cop 1.

SUMMARY OF THE INVENTION

The present invention is based on the surprising discovery that not only is Copolymer 1 useful for the treatment of GVHD, but it is also useful for the treatment of HVGD. Furthermore, heteropolymers other than the specific composition of Copolymer 1 can be used both for the GVHD indication and for the HVGD indication.

Thus, the present invention provides a pharmaceutical composition for use in the prevention and treatment of graft-versus-host disease and host-versus-graft disease comprising random heteropolymers of amino acids. The polymers comprise random copolymers comprising a suitable quantity of an amino acid of positive electrical charge, such as lysine or arginine, in combination with an amino acid with a negative electrical charge (preferably in a lesser quantity), such as glutamic acid or aspartic acid, optionally in combination with an electrically neutral amino acid such as alanine or glycine, serving as a filler, and optionally with an amino acid adapted to confer on the copolymer immunogenic properties, such as an aromatic amino acid like tyrosine or tryptophan. As Copolymer 1 (all L) and D-Copolymer 1 (all D) are already known for the treatment of GVHD, the present invention specifically excludes both Copolymer 1 and D-Copolymer 1 when the indication is GVHD.

More specifically, the pharmaceutical composition for use in preventing and treating graft-versus-host disease (GVHD) and host-versus-graft disease (HVGD) comprises at least one copolymer selected from the group consisting of random copolymers comprising one amino acid selected from each of at least three of the following groups:

(a) lysine and arginine;
(b) glutamic acid and aspartic acid;
(c) alanine and glycine;
(d) tyrosine and tryptophan, provided that the copolymer is not Copolymer 1 or D-Copolymer 1 when the disease being treated is GVHD.

In one embodiment of the invention, the copolymer contains four different amino acids each from one of the groups (a) to (d). A preferred copolymer according to this embodiment of the present invention comprises in combination alanine, glutamic acid, lysine, and tyrosine, of net overall positive electrical charge and of a molecular weight of about 2,000 to about 40,000 daltons, preferably of about 2,000 to about 13,000 daltons. The most preferred example is Copolymer 1 of average molecular weight of about 4,700 to about 13,000 daltons. It is clear that this is given by way of example only, and that the composition can be varied both with respect to the constituents and relative proportions of the constituents if the above general criteria are adhered to.

In another embodiment, the copolymer contains three different amino acids each from one of three groups of the groups (a) to (d). These copolymers are herein referred to as terpolymers.

Thus, the present invention is also directed to pharmaceutical compositions which include a therapeutically effective amount of a random terpolymer consisting essentially of amino acids tyrosine (or tryptophan), alanine (or glycine) and lysine (or arginine), preferably tyrosine, alanine and lysine, in the molar ratio of from about 0.005 to about 0.25 tyrosine, from about 0.3 to about 0.6 alanine, and from about 0.1 to about 0.5 lysine, along with a pharmaceutically acceptable carrier. This terpolymer, hereinafter designated YAK, is preferably substantially free of glutamic acid.

The present invention further provides a pharmaceutical composition which includes a therapeutically effective amount of a random terpolymer consisting essentially of glutamic acid (or aspartic acid), tyrosine (or tryptophan), and lysine (or arginine), preferably glutamic acid, tyrosine, and lysine, in the molar ratio of from about 0.005 to about 0.300 glutamic acid, from about 0.005 to about 0.250 tyrosine, and from about 0.3 to about 0.7 lysine, and a pharmaceutically acceptable carrier. This terpolymer, hereinafter designated YEK, is preferably substantially free of alanine.

The present invention is also directed to pharmaceutical compositions which include a therapeutically effective amount of a random terpolymer consisting essentially of the amino acids tyrosine (or tryptophan), glutamic acid (or aspartic acid) and alanine (or glycine), preferably tyrosine, glutamic acid and alanine, in the molar ratio of from about 0.005 to about 0.25 tyrosine, from about 0.005 to about 0.3 glutamic acid, and from about 0.005 to about 0.8 alanine, and a pharmaceutically acceptable carrier. This terpolymer, hereinafter designated YEA, is preferably substantially free of lysine.

The present invention also provides a pharmaceutical composition which includes a therapeutically effective amount of a random terpolymer consisting essentially of glutamic acid (or aspartic acid), alanine (or glycine) and lysine (or arginine), preferably glutamic acid, alanine and lysine, in the molar ratio of from about 0.005 to about 0.3 glutamic acid, from about 0.005 to about 0.6 alanine, and from about 0.2 to about 0.7 lysine, and a pharmaceutically acceptable carrier. This terpolymer, herein after designated KEA, is preferably substantially free of tyrosine.

The present invention further provides methods for treating and preventing GVHD or HVGD in a mammal by administering a therapeutically effective amount of a composition comprising at least one copolymer selected from the group consisting of random copolymers comprising one amino acid from at least three or four of the following groups:

(a) lysine and arginine;
(b) glutamic acid and aspartic acid;
(c) alanine and glycine;
(d) tyrosine and tryptophan provided that the random copolymer is not Copolymer 1 or D-Copolymer 1 when the disease is GVHD.

The prevention and/or treatment of graft rejection contemplated by the present invention includes transplantation of organs or tissues from HLA matched and unmatched allogeneic human donors, or xenografts from donors of other species. Such transplanted grafts include hearts, lungs, kidneys, livers, skin and other organs or tissues transplanted from donor to recipient.

Therapeutically effective amounts of Copolymer 1, according to the present invention, are about 1.0 mg to about 500.0 mg. Preferably, such therapeutically effective amounts of Copolymer 1 are about 20.0 mg to about 100.0 mg.

The copolymers used in the present invention preferably have an average molecular weight of about 5,500–10,000 Da, more preferably of 6,000–8,000 Da, and most preferably, of about 6,000 or of about 8,000. For the purposes of the present invention, terpolymers comprised of these amino acids will also be referred to as copolymers.

The amino acid residues of the groups (a) to (d) above may all have the L-configuration or the D configuration or some of the residues may have the L- and the others the D-configuration.

When the copolymer consists of the Glu, Lys, Ala and Tyr residues, preferred molar ratios of the amino acid residues include the relative molar ratios 1.7 Glu to 3.8 Lys to 4.9 Ala to 1.0 Tyr, and 1.9 Glu to 4.0 Lys to 6.0 Ala to 1 Tyr.

Although the present specification describes some preferred embodiments of the invention, it is to be understood that the present invention encompasses the use of any synthetic random copolymer of at least three of Glu or Asp, Lys or Arg, Ala or Gly, and Tyr or Trp, having a relative molar ratio of the amino acid residues and an average molecular weight as defined herein, including those forms of Cop 1 described in the literature that fall within the definition of the present invention, but excluding Copolymer 1 and D-Copolymer 1 for the treatment of GVHD.

In another aspect, the invention relates to the use of the random copolymers described above for the manufacture of a medicament for prevention and treatment of graft-versus-host disease or host-versus-graft disease, but excluding Copolymer 1 and D-Copolymer 1 for the treatment of graft-versus-host disease.

In a further embodiment, the invention relates to a method of treatment of a patient for prevention and treatment of graft-versus-host disease and/or host-versus-graft disease in the course of bone marrow and organ transplantation, said method comprising administering to said patient effective amounts of said random copolymers, but excluding Copolymer 1 and D-Copolymer 1 for the treatment of Graft-versus-host disease.

In a preferred embodiment, the random copolymer is used according to the invention for prevention of Graft-versus-host disease and/or Host-versus-graft disease in allogeneic bone marrow transplantation, optionally together with other immunosuppressive agents.

The preferred copolymer according to the present invention for the treatment of HVGD is Copolymer 1.

DETAILED DESCRIPTION OF THE INVENTION

The random copolymers used in the present invention represent a novel therapeutic approach to treat human host-versus-graft disease for effective organ transplantation. Furthermore, a broader class of random copolymers than the previously disclosed Copolymer 1 is presented for the treatment of Graft-versus-host disease, particularly with regard to bone marrow transplantation.

The copolymers for use in the present invention can be composed of L- or D-amino acids or mixtures thereof. As is known by those of skill in the art, L-amino acids occur in most natural proteins. However, D-amino acids are commercially available and can be substituted for some or all of the amino acids used to make the terpolymers and other copolymers of the present invention. The present invention contemplates copolymers containing both D- and L-amino acids, as well as copolymers consisting essentially of either L- or D-amino acids.

The average molecular weight and the average molar fraction of the amino acids in the copolymers can vary. However, a molecular weight range of about 2,000 to 40,000 daltons is contemplated. A preferred molecular weight range is from about 2,000 to about 12,000 daltons. The copolymers can be from about 15 to about 100, preferably from about 40 to about 80, amino acids in length. Preferred molecular weight ranges and processes for making a preferred form of Copolymer 1 is described in U.S. Pat. No. 5,800,808, the entire contents of which being hereby incorporated in the entirety.

In one embodiment, the terpolymers for use in the present invention contain tyrosine, alanine, and lysine, hereinafter designated YAK. The average molar fraction of the amino aids in these terpolymers can vary. For example, tyrosine can be present in a mole fraction of about 0.005 to about 0.250; alanine can be present in a mole fraction of about 0.3 to about 0.6; and lysine can be present in a mole fraction of about 0.1 to about 0.5. The average molecular weight is between 2,000 to about 40,000 daltons, and preferably between about 3,000 to about 35,000 daltons. In a more preferred embodiment, the average molecular weight is about 5,000 to about 25,000 daltons. It is possible to substitute arginine for lysine, glycine for alanine, and tryptophan for tyrosine.

In another embodiment, the terpolymers for use in the present invention contain tyrosine, glutamic acid, and lysine, hereinafter designated YEK. The average molar fraction of the amino acids in these terpolymers can vary: glutamic acid can be present in a mole fraction of about 0.005 to about 0.300, tyrosine can be present in a mole fraction of about 0.005 to about 0.250, and lysine can be present in a mole fraction of about 0.3 to about 0.7. The average molecular weight is between 2,000 and about 40,000 daltons, and preferably between about 3,000 and about 35,000 daltons. In a more preferred embodiment, the average molecular weight is about 5,000 to about 25,000 daltons. It is possible to substitute aspartic acid for glutamic acid, arginine for lysine, and tryptophan for tyrosine.

In another embodiment the terpolymers for use in the present invention contain lysine, glutamic acid, and alanine, hereinafter designated KEA. The average molar fraction of the amino acids in these polypeptides can also vary. For example, glutamic acid can be present in a mole fraction of about 0.005 to about 0.300, alanine can be present in a mole fraction of about 0.005 to about 0.600, lysine can be present in a mole fraction of about 0.2 to about 0.7. The average molecular weight is between 2,000 and 40,000 daltons, and preferably between about 3,000 and 35,000 daltons. In a more preferred embodiment, the average molecular weight is about 5,000 to about 25,000 daltons. It is possible to substitute aspartic acid for glutamic acid, glycine for alanine, and arginine for lysine.

In another embodiment, the terpolymers for use in the present invention contain tyrosine, glutamic acid, and alanine, hereinafter designated YEA. The average molar fraction of the amino acids in these polypeptides can vary. For example, tyrosine can be present in a mole fraction of about 0.005 to about 0.250, glutamic acid can be present in a mole fraction of about 0.005 to about 0.300, and alanine can be present in a mole fraction of about 0.005 to about 0.800. The average molecular weight is between 2,000 and about 40,000 daltons, and preferably between about 3,000 and about 35,000 daltons. In a more preferred embodiment, the average molecular weight is about 5,000 to about 25,000 daltons. It is possible to substitute tryptophan for tyrosine, aspartic acid for glutamic acid, and glycine for alanine.

In a more preferred embodiment, the mole fraction of amino acids of the terpolymers is about what is preferred for Copolymer 1. The mole fraction of amino acids in Copolymer 1 is glutamic acid about 0.14, alanine about 0.43, tyrosine about 0.10, and lysine about 0.34. The most preferred average molecular weight for Copolymer 1 is between about 5,000 and about 9,000 daltons. The activity of Copolymer 1 both in the treatment of GVHD and HVGD is expected to remain if one or more of the following substitutions is made: aspartic acid for glutamic acid, glycine for alanine, arginine for lysine, and tryptophan for tyrosine.

The molar ratios of the monomers of the more preferred terpolymer of glutamic acid, alanine, and tyrosine, or YEA, is about 0.21 to about 0.65 to about 0.14.

The molar ratios of the monomers of the more preferred terpolymer of glutamic acid, alanine and lysine, or KEA, is about 0.15 to about 0.48 to about 0.36.

The molar ratios of the monomers of the more preferred terpolymer of glutamic acid, tyrosine, and lysine, or YEK, is about 0.26 to about 0.16 to about 0.58.

The molar ratios of the monomers of the more preferred terpolymer of tyrosine, alanine and lysine, or YAK, is about 0.10 to about 0.54 to about 0.35.

For purposes of the present invention, the random copolymers described herein specifically exclude Copolymer 1 µg when the indication is GVHD. If necessary, the random copolymers may exclude any random mixture of heteropolymers containing all of glutamic acid, lysine, alanine and tyrosine.

For the host-versus-graft disease indication (transplant/graft rejections) the preferred active principle is Copolymer 1. Thus, in its preferred form, the present invention is directed to a pharmaceutical composition for the prevention and treatment of graft rejection, which includes a therapeutically effective amount of Copolymer 1 and a pharmaceutically acceptable carrier.

The present invention in a further preferred embodiment is directed to methods for preventing and treating graft rejection which includes administering a therapeutically effective amount of Cop 1.

According to the present invention, the limitations of currently available immunosuppression therapies used in patients about to undergo bone marrow or organ transplantation are overcome by use of Copolymer 1 and other random copolymers as described herein. Copolymer 1 has been approved in several countries for the treatment of Multiple Sclerosis (MS) under the trade name, COPAXONE®, Glatiramer acetate. Several clinical trials demonstrated that Copolymer 1 is well tolerated with only minor side reactions which were mostly mild reactions at the injection site (Johnson et al., 1995).

Copolymer 1 binds promiscuously and with high affinity to various class II MHC molecules from mouse and human origin, and can even displace antigens from the MHC groove (Fridkis-Hareli et al., 1994). Mixed lymphocyte reaction, which is used clinically to assess immune rejection between donors and recipients, is also inhibited by Copolymer 1 (Schlegel et al., 1996).

When tissue from donor mice is transplanted to recipient mice, immune rejection generally occurs. This is manifested either by GVHD in bone marrow transplantation or graft rejection in organ transplantation.

Copolymer 1 and D-Copolymer 1 were shown to prevent GVHD in a murine model of lethal GVHD which mimics matched bone marrow transplantation in humans (see U.S. Pat. No. 5,858,964, and particularly FIGS. 4 and 5 thereof, and FIG. 3 of Schlegel et al., 1996). According to the present invention, random copolymers other than Copolymer 1 and D-Copolymer 1 are envisaged for use in the prevention and treatment of GVHD.

According to the present invention, Copolymer 1, D-Copolymer 1 and other random copolymers are envisaged to prevent or significantly delay graft rejection. As shown in the Examples hereinafter, Copolymer 1 is effective in suppressing in mice the rejection of grafts received from another mouse strain of the same MHC haplotype. Thus, graft rejection could be suppressed in BALB/c mice receiving grafts from B10.D2 donor mice, in C3HSH mice receiving grafts from C57BL donor mice, and in PJL mice receiving grafts from B10PL donor mice (see Tables 4 and 5 herein). These transplantation mouse models are similar to the MHC matched organ transplantation in humans. Moreover, Copolymer 1 is also effective in suppressing in mice rejection of grafts from strains of different MHC haplotypes, for example, suppressing in BALB/c mice rejection of grafts received from C57BL donor mice (see Tables 4 and 5 herein), a model which is similar to the MHC unmatched organ transplantation in humans. Thus, pre- and post-transplantation administration of Copolymer 1 over a limited time after transplantation can significantly reduce the incidence, onset and severity of immunorejection, resulting in improved long-term survival.

As described before for the mechanism of action for GVHD (Aharoni et al., 1993), Copolymer 1 inhibits T cell proliferation in response to host cells. Copolymer 1 treatment completely abolished cytotoxic activity towards host cells, preventing the secretion of cytokines like interleukin 2 (IL-2) and interferon γ (IFN-γ), and induced a beneficial anti-inflammatory response. Similar effects can occur in graft rejection disease.

The present invention is also directed to the use of terpolymers as defined herein for the prevention and treatment of GVHD and HVGD. The terpolymers can be made by any procedure available to one of skill in the art. For example, the terpolymers can be made under condensation conditions using the desired molar ratio of amino acids in solution, or by solid phase synthetic procedures. Condensation conditions include the proper temperature, pH, and solvent conditions for condensing the carboxyl group of one amino acid with the amino group of another amino acid to form a peptide bond. Condensing agents, for example dicyclohexyl-carbodiimide, can be used to facilitate the formation of the peptide bond. Blocking groups can be used to protect functional groups, such as the side chain moieties and some of the amino or carboxyl groups against undesired side reactions.

For example, the process disclosed in U.S. Pat. No. 3,849,650, can be used wherein the N-carboxyanhydrides of tyrosine, alanine, γ-benzyl glutamate and N ε-trifluoroacetyl-lysine are polymerized at ambient temperatures in anhydrous dioxane with diethylamine as an initiator. The γ-carboxyl group of the glutamic acid can be deblocked by hydrogen bromide in glacial acetic acid. The trifluoroacetyl groups are removed from lysine by 1 molar piperidine. One of skill in the art readily understands that the process can be adjusted to make peptides and polypeptides containing the desired amino acids, that is, three of the four amino acids in Copolymer 1, by selectively eliminating the reactions that relate to any one of glutamic acid, alanine, tyrosine, or lysine. For purposes of this application, the terms "ambient temperature" and "room temperature" mean a temperature ranging from about 20 to about 26° C.

The molecular weight of the terpolymers can be adjusted during polypeptide synthesis or after the terpolymers have been made. To adjust the molecular weight during polypeptide synthesis, the synthetic conditions or the amounts of amino acids are adjusted so that synthesis stops when the polypeptide reaches the approximate length which is desired. After synthesis, polypeptides with the desired molecular weight can be obtained by any available size selection procedure, such as chromatography of the polypeptides on a molecular weight sizing column or gel, and collection of the molecular weight ranges desired. The present polypeptides can also be partially hydrolyzed to remove high molecular weight species, for example, by acid or enzymatic hydrolysis, and then purified to remove the acid or enzymes.

In one embodiment, the terpolymers with a desired molecular weight may be prepared by a process which includes reacting a protected polypeptide with hydrobromic acid to form a trifluoroacetyl-polypeptide having the desired molecular weight profile. The reaction is performed for a time and at a temperature which is predetermined by one or more test reactions. During the test reaction, the time and temperature are varied and the molecular weight range of a given batch of test polypeptides is determined. The test conditions which provide the optimal molecular weight range for that batch of polypeptides are used for the batch. Thus, a trifluoroacetyl-polypeptide having the desired molecular weight profile can be produced by a process which includes reacting the protected polypeptide with hydrobromic acid for a time and at a temperature predetermined by test reaction. The trifluoroacetyl-polypeptide with the desired molecular weight profile is then further treated with an aqueous piperidine solution to form a low toxicity polypeptide having the desired molecular weight.

In a preferred embodiment, a test sample of protected polypeptide from a given batch is reacted with hydrobromic acid for about 10–50 hours at a temperature of about 20–28° C. The best conditions for that batch are determined by running several test reactions. For example, in one embodiment, the protected polypeptide is reacted with hydrobromic acid for about 17 hours at a temperature of about 26° C.

The random copolymers used in the present invention can be formulated into pharmaceutical compositions containing a pharmaceutically acceptable carrier. As used herein, "pharmaceutically acceptable carrier" includes any and all solvents, dispersion media, coatings, antibacterial and antifungal agents, isotonic and absorption delaying agents, sweeteners and the like. The pharmaceutically acceptable carriers may be prepared from a wide range of materials including, but not limited to diluents, binders and adhesives, lubricants, disintegrants, coloring agents, bulking agents, flavoring agents, sweetening agents and miscellaneous materials such as buffers and absorbents that may be needed in order to prepare a particular therapeutic composition. The use of such media and agents with pharmaceutically active substances well known in the art. Except insofar as any conventional media or agent is incompatible with the active ingredient, its use in the therapeutic compositions is contemplated.

The present compositions are formulated into any form known in the art using procedures available to one of skill in the art.

The invention will now be illustrated by the following non-limiting examples.

EXAMPLES

Materials and Methods
(a) Preparation of Copolymer 1 and Controls
(i) Copolymer 1/L-GLAT, was prepared by polymerization of the N-carboxyanhydrides of L-Ala, γ-benzyl-L-Glu, N,ε-trifluoroacetyl-L-Lys, and L-Tyr. The polymerization reaction was carried out at room temperature in anhydrous dioxane with diethylamine as initiator. Deblocking of the γ-carboxyl groups of the glutamic acid was carried out with hydrogen bromide in glacial acetic acid for 24 hours at room temperature, followed by removal of the trifluoroacetyl groups from the lysine residue by 1M piperidine. The end product is a mixture of acetate salts of random polypeptides with amino acid composition of Ala (4.1–5.8 residues), Glu (1.4–1.8 residues), Lys (3.2–4.2 residues), Tyr (1 residue). Two L-GLAT batches were used in the experiments of GVHD: Batch I consisting of a copolymer of molecular weight of about 6,000, with the amino acids in the molar ratio of about 1.7 Glu to 3.8 Lys to 4.9 Ala to 1.0 Tyr, and Batch II, consisting of a copolymer of molecular weight of about 8,000, with the amino acids in the molar ratio of 1.8 Glu to 4.0 Lys to 6.0 Lys to 1.0 Tyr. For the experiments of HVGD, two batches of Copolymer 1 were kindly provided by Teva Pharmaceutical Industries Ltd., Israel: Batch III consisting of a copolymer of molecular weight of about 5,800, with the amino acids in the molar ratio of about 1.5 Glu to 3.7 Lys to 4.8 Ala to 1.0 Tyr, and Batch IV, consisting of a copolymer of molecular weight of about 7,150, with the amino acids in the molar ratio of 1.5 Glu to 3.2 Lys to 4.5 Ala to 1.0 Tyr.

(ii) D-GLAT was prepared by polymerization of the N-carboxyanhydrides of the D-amino acids D-Ala, γ-benzyl-D-Glu, N,ε-trifluoroacetyl-D-Lys, and D-Tyr in a residue molar ratio of 5.6:2.2:4.6:1.0 with an average molecular weight of approx. 29,000.

(iii) TGA or YEA is a random basic polymer of L-Tyr, γ-benzyl-L-Glu, and L-Ala in a residue molar ratio of 1.0:1.2:1.1. It was used as a negative control.

(iv) Hen egg-white lysozyme (HEL) was obtained from Sigma Chemical Company (St. Louis, Mo.).

(v) The following peptides were synthesized by standard Fmoc chemistry. All peptides were 95% to 99% pure, as determined by high-performance liquid chromatography, and were checked by amino acid analysis and mass spectroscopy. Sequences are given in single letter codes:

MBP Ac1-11[4A], an acetylated N-terminal 1-11 peptide of myelin basic protein (MBP), with substitution of the original Lys residue at position 4 by Ala: ACASQARPSQRHG (SEQ ID NO:1);

MBP 35-47, the epitope of MBP which is recognized in association with I-Eu: TGILDSIGRFFSG (SEQ ID NO:2);

KM-core extension peptide, based on the antigenic core sequence of ovalbumin 323–339: KMKMVAAHAK-MKM (SEQ ID NO:3);

MBP 89-101: VHFFKNIVTPRTP (SEQ ID NO:4), was synthesized by t-butoxy-carbonyl chemistry.

(b) Animals

B10.D2/nSnJ (H-$2^d$), CBA (H-$2^k$), C57BL/6 and C3H (H-$2^b$), B10.PL and PL/J (H-$2^u$) mice were purchased from Jackson Laboratories (Bar Harbor, Me.); BALB/c (H-$2^d$) recipient mice were obtained from Simonsen Laboratories (Gilroy, Calif.) or from Jackson Laboratories.

(c) Mixed Lymphocyte Reaction (MLR)

Responder cells for MLR reactions across major histocompatibility barriers were harvested from spleen of non-immunized mice while responder cells for MLR across minor histocompatibility barriers were harvested from mice which were preimmunized with irradiated (30 Gy) $50 \times 10^6$ stimulator spleen cells 21 days before. Responder cells ($5 \times 10^5$ spleen cells per well) were tested for their proliferative response by plating with different amounts (2.5 to $10 \times 10^5$) of irradiated stimulator cells, in presence or absence of various peptide inhibitors (10–100 μg per well). Cultures were set up in 200 μl media containing 10% FCS in flat-bottom microtiter plates. After 4 days of incubation, cultures were pulsed with 1 μCi of [$^3$H]thymidine for an additional 16 hours. Results are represented as mean counts per minute (cpm) thymidine incorporation from triplicate cultures.

(d) Bone Marrow Transplantation

The murine GVHD model of B10.D2/nSnJ→BALB/c mice (both H-$2^d$) across minor histocompatibility barriers, was selected since it is similar to the MHC matched bone marrow transplantation in humans. For the induction of GVHD, $10 \times 10^6$ bone marrow and $100 \times 10^6$ spleen cells from B10.D2 mice were injected into lethally irradiated (8.0 Gy) BALB/c recipients. This regimen induces the most severe form of GVHD (Schlegel et al., 1996) and was selected for all experiments of GVHD. Recipient mice were 12–13 weeks at the time of transplantation.

(e) PCR Analysis

Engraftment of donor bone marrow was documented by PCR amplification of a polymorphic microsatellite region within the murine IL-1b gene. Primer sequences are as follows: 5'-CCAAGCTTCCTTGTGCAAGTA-3' (SEQ ID NO:5) and 5'-AAGCCCAAAGTCCATCAGTGG-3' (SEQ ID NO:6) (Jacob et al., 1993). These sequences are available from EMBL/Gen-Bank/DDBJ database (Bethesda, Md.) under the accession numbers: X78456 and X78457. Oligonucleotides were synthesized on a 391 DNA synthesizer (Applied Biosystems, Foster City, Calif.) and were purified. DNA was prepared from peripheral blood mononuclear cells 80–120 days after transplantation according to standard protocols. PCR conditions and amplification were as described previously (Schlegel et al., 1994).

(f) Treatment of GVHD

Recipient BALB/c mice were treated with Copolymer 1, PBS, or with HEL. Based on previous studies with Cop 1 in EAE (Sela et al., 1990; Teitelbaum et al., 1971; Teitelbaum et al., 1973) and class II-binding competitor peptides in GVHD (Schlegel et al., 1994), the dosage of 600 μg per injection was selected, half of which was administered intraperitoneally (ip), whereas the other half was given subcutaneously (sc). Treatment of BALB/c recipient mice was initiated on day −1, followed by daily injections for the first five weeks starting on day 0 after transplantation. The frequency of injections was tapered to three times per week for the subsequent two weeks and to two times per week for another two weeks and then discontinued. Throughout the experiment, copolymers and controls were administered once a week with incomplete Freund's adjuvant (IFA) ip as a depot dose (Schlegel et al., 1994). Treatment was discontinued 9 weeks after transplantation.

(g) Assessment of GVHD

Mice were followed up daily for 140 days after bone marrow transplantation for signs of GVHD. Disease severity was assessed by mortality, loss of body weight, and by the extent of macroscopic skin involvement scored on a cumulative scale (from min 0— max 8): head 1, neck 1, back (1/3, 2/3, 3/3) 1–3, front (1/3, 2/3, 3/3) 1–3. Skin biopsies were examined as previously described (Schlegel et al., 1994).

(h) Inhibition of Minor Histocompatibility (mH) Antigen Presentation

B10.D2 mice were injected ip. with irradiated (20 Gy) BALB/c spleen cells 72 hours prior to the assay. B10.D2 spleen cells were harvested, depleted of red blood cells (RBC) and used as irradiated (10 Gy) antigen-presenting cells (APC) presenting BALB/c mH antigens. For the primary assay, APC were plated at $2.5 \times 10^5$ cells per well in 96-well round-bottom plates and incubated with $2.5 \times 10^5$ nylon-wool-enriched responder T cells (>88% CD3$^+$ by FACS analysis) from naive B10.D2 mice in the presence or absence of increasing concentrations of Copolymer 1 (2.5–80 μg/well). After 96 hours of incubation, cells were pulsed with 1 μCi [$^3$H]-thymidine for an additional 16 hours before harvesting. In the secondary assay, irradiated APC were plated at $2.5 \times 10^5$ cells/well in 96-well round-bottom plates, preincubated for 24 hours at 37° C. with increasing concentrations of GLAT (2.5–80 μg/well) or with medium alone, and thereafter washed three times before the addition of $2.5 \times 10^5$ nylon-wool-enriched responder T cells from naive B10.D2 mice. Culture medium was RPMI 1640, supplemented with 10% pre-screened fetal calf serum, 2 mM glutamine, 50 μM 2-mercaptoethanol, 100 U/ml penicillin, and 100 μg/ml streptomycin.

(i) Skin Grafts Transplantation Model System for HVGD

Skin graft rejection is a vigorous process, more difficult to suppress than the rejection of other organs (Isakov et al., 1979). This may be due to the high expression of MHC molecules in this tissue. The ability to postpone this rejection process is therefore significant. Recipient mice were dorsally transplanted with circular pieces of donor skin. Mice were inspected daily. Grafts were considered rejected when no viable donor epidermis remained. The results are expressed in mean survival time (MST). P values were obtained by analysis of variance (ANOVA).

(j) Thyroid Graft Assay

In this transplantation model for HVGD, thyroid glands from donor mice were transplanted in the kidney's capsules of recipient mice. One week later the transplanted mice were injected with $^{125}$I, and the radioactivity of each kidney (the recipient or the untransplanted kidney) was measured after 20 hours. Δcpm was calculated by subtracting the $^{125}$I absorbance of the untransplanted kidneys from the $^{125}$I absorbance of the recipient kidneys in the same treatment. The mean function index (MFI) for treatment was calculated by dividing the mean Δcpm for the tested (Copolymer 1) treatment by the mean Δcpm for the PBS treatment. P values were obtained by the t test. This assay indicates objectively and quantitatively not only the graft survival, but also the function (iodine absorbance) of the transplanted thyroid tissue (Isakov et al., 1979).

(k) Copolymer 1 Treatment for HVGD

The transplanted mice were treated daily with Copolymer 1 600 μg/day (300 μg ip+300 μg sc) in PBS solution, starting 7 days before transplantation. The first Cop 1 treatment on day −7 was injected sc in ICFA as a depot dose. Control mice were treated daily with PBS alone and PBS with ICFA on day −7 before transplantation.

Example 1

Inhibition of Mixed Lymphocyte Reaction by Cop 1

This example demonstrates the inhibition of mixed lymphocyte reaction (MLR) by Copolymer 1 and is presented here for illustration only. MLR, the proliferative response of allogeneic lymphocytes when cultured together, is considered an in vitro model for the recognition phase of the GVHD reaction, and is part of the routine screening for bone marrow donors.

To investigate the feasibility of inhibition of MLR by Copolymer 1, an MLR system was developed in which Copolymer 1 was tested for its ability to inhibit the proliferation of B10.PL (H-$2^u$) responder cells to stimulator cells of either the same (PL/J) or different (BALB/c) H-2 haplotype. For comparison, the inhibitory MBP Ac 1-11[4A], MBP 35-47, a combination of Ac 1-1[4A]+MBP 35-47, MBP 89-101 and KM-core peptides, described in Schlegel et al. (1994), were used in the MLR experiments.

As shown in FIG. 1A of U.S. Pat. No. 5,858,964 for stimulator cells of PL/J mice and in FIG. 1B of that patent for stimulator cells of BALB/c mice, Copolymer 1 (Batch I; 20 μg/well) significantly inhibited MLR across minor as well as major histocompatibility barriers. 63% and 77% inhibition could be obtained, respectively, when 1:1 ratio of responder to stimulator cells was used, while the MBP 89-101 and the M-core peptides (at the same concentration, i.e. 20 μg/well), which are specific to the H-$2^s$ haplotype, did not induce any significant effect. The inhibition obtained by Copolymer 1 was similar (in response to minor histocompatibility antigen) or even higher (in response to major histocompatibility antigen) than the inhibition obtained with the combination of the two synthetic peptides Ac 1-11[4A] and MBP 35-47, which specifically bind to the class II molecules I-$A^u$ and the I-$E^u$, respectively. The molar efficiency of Copolymer 1 of M.W. 6000 is even higher since the molecular weight of the synthetic peptides is 4–5 fold lower.

Example 2

Inhibition of MLR across Major Histocompatibility Barriers

The effect of Copolymer 1 (Batch I) on mixed lymphocyte cultures across major histocompatibility barriers was tested. T cell proliferation was assessed in six different MHC-disparate strain combinations. Data given in FIGS. 1A–1E of Schlegel et al. (1996) are representative of five separate experiments with similar results. In all experiments, addition of Copolymer 1 (10–100 μg/well) resulted in a dose-dependent inhibition of the MLC. HEL showed no or only minimal inhibitory effect at all concentrations tested (FIGS. 1A–1E of Schlegel et al., 1996). 10–25 μg/well of Copolymer 1 was sufficient to achieve 50% inhibition of the proliferative responses. Maximum inhibition (100%) was obtained in all strain combinations tested. To exclude the possibility that higher concentrations of Copolymer 1 (50–100 μg/well) might be toxic to the responder cells, responder cells from background well and from wells incubated with 25–100 μg/well of Copolymer 1 in the presence of stimulator cells for 72 hours in a primary assay, were rechallenged in a subsequent secondary assay with IL-2 (5,000 U/well). As shown in Table 1, there was no difference between the secondary proliferative responses of the groups tested. Responder cells that had been incubated with stimulator cells in the presence of Copolymer 1 for 72 hours were equally responsive to IL-2 compared to non-treated cells.

TABLE 1

Effect of Incubation with Different Concentrations of Copolymer 1 on the Subsequent Proliferative Response to Re-stimulation with IL-2

| Primary Responder | Assay[1] Stimulator | Cop 1 (μg/well) | cpm | Secondary Stimulus | Assay[2] cpm |
|---|---|---|---|---|---|
| B10.D2 | — | — | 564 | IL-2 | 9,170 |
| B10.D2 | C57BL/6 | — | 20,333 | IL-2 | 8,305 |
| B10.D2 | C57BL/6 | 100 μg | 283 | IL-2 | 7,951 |
| B10.D2 | C57BL/6 | 50 μg | 3,663 | IL-2 | 15,123 |
| B10.D2 | C57BL/6 | 25 μg | 15,953 | IL-2 | 11,994 |

[1]Primary Assay (left): 2.5 × 10$^5$ responder spleen cells were incubated with 2.5 × 10$^5$ irradiated (30 Gy) spleen stimulator cells in a final volume of 200 μl in the presence or absence of Copolymer 1 (Batch I) as indicated. After 96 hours of incubation, cultures were pulsed with 1 μCi [$^3$H]-thymidine for an additional 16 hours.
[2]Secondary assay (right): Identical cultures were set up in parallel to the primary assay. After 72 hours of incubation, responder cells were rechallenged with IL-2 (5,000 U/well) for an additional 48 hours before pulsing with 1 μCi [$^3$H]-thymidine for an additional 16 hours. Results are expressed as mean cpm from triplicate cultures. Standard deviations were less <16% of the mean.

Example 3

Inhibition of Proliferative Responses to Minor H Antigens In Vitro

B10.D2 mice were injected ip with irradiated (20 Gy) BALB/c spleen cells 72 hours prior to the assay. B10.D2 spleen cells were harvested, depleted of RBC and used as irradiated (10 Gy) APC presenting BALB/c mH antigens. APC were plated at 2.5×10$^5$ cells/well in 96-well round-bottom plates and incubated with 2.5×10$^5$ nylon-wool-enriched responder T cells (>88% CD3$^+$ by FACS analysis) from naive B10.D2 mice in the presence or absence of increasing concentrations of Copolymer 1 (Batch I) (2.5–80 μg/well). After 96 hours of incubation, cells were pulsed with 1 μCi [$^3$H]-thymidine for an additional 16 hours before harvesting. As shown in Table 2, left, Copolymer 1 (Batch II) inhibited the proliferative responses to mH antigens in a dose-dependent fashion. Maximum inhibition was 100% at a concentration of 80 μg/well.

To further elucidate the mechanism of inhibition, a second experiment was carried out: irradiated (20 Gy) APC were plated at 2.5×10$^5$ cells/well in 96-well round-bottom plates, preincubated for 24 hours at 37° C. with increasing concentrations of Copolymer 1 (Batch II) (2.5–80 μg/well) or with medium alone, and thereafter washed three times before the addition of 2.5×1 0$^5$ nylon wool-enriched responder T cells from naive B10.D2 mice. Results are expressed as cpm from triplicate cultures. Standard deviations were <20% of the mean. Culture medium was RPMI 1640, supplemented with 10% pre-screened fetal calf serum, 2 mM glutamine, 50 μM 2-mercaptoethanol, 100 U/ml penicillin, and 100 μg/ml streptomycin. As shown in Table 2, right, preincubation with Copolymer 1 inhibited proliferative responses to minor H antigens, suggesting that Copolymer 1 inhibits presentation of minor antigens in vitro.

TABLE 2

Dose-dependent inhibition of proliferative responses to minor H antigens

| Resp. | APC | Cop 1 Assay Concentration | cpm | Resp. | APC | Pre-pulsed APC | Cop 1 Pulsing Concentration | cpm |
|---|---|---|---|---|---|---|---|---|
| + | − | — | 10,464 | + | + | − | — | 7,855 |
| + | + | — | 108,574 | + | + | − | — | 16,724 |
| + | + | 80 µg | 361 | + | − | + | 80 µg | 4,628 |
| + | + | 40 µg | 23,591 | + | − | + | 40 µg | 7,653 |
| + | + | 20 µg | 75,840 | + | − | + | 20 µg | 10,465 |
| + | + | 10 µg | 119,866 | + | − | + | 10 µg | 11,425 |
| + | + | 5 µg | 126,405 | + | − | + | 5 µg | 12,377 |
| + | + | 1.5 µg | 124,904 | + | − | + | 1.5 µg | 15,533 |

Example 4

Bone Marrow Transplantation in Mice, Induction of GVHD and Treatment with Copolymer 1

(i) Initial Titration Study. For the induction of GVHD across minor histocompatibility barriers, an initial titration study was performed by transplanting $10 \times 10^6$ B10.D2 bone marrow cells and increasing amounts ($10-100 \times 10^6$) of B10.D2 spleen cells into lethally irradiated (8.0 Gy) 12–13 week old BALB/c recipients. The regimen of infusing $10 \times 10^6$ bone marrow cells and $100 \times 10^6$ spleen cells resulted in the most severe form of GVHD, and was selected for all subsequent experiments.

(ii) Effect of Copolymer 1 Treatment on the Incidence, Onset and Severity of GVHD. Recipient mice were pre-treated with 600 µg of Copolymer 1 (Batch I) or with the respective controls (PBS, HEL) on day −1. For the first five weeks after transplant mice were injected daily as outlined in Materials and Methods, followed by a tapering schedule over an additional four weeks. Data from three consecutive experiments are summarized in FIGS. 3A–D of Schlegel et al. (1996). Administration of Copolymer 1 significantly reduced the overall incidence of GVHD (as determined by typical skin changes and weight loss) from 100% (26/26, 10/10) in control mice to 12% (3/25) (P<0.001) in Copolymer 1-treated animals on day 30 after transplant and from 100% in controls to 12/25 (48%) on day 70 after transplant (P>0.02). FIG. 3A of Schlegel et al. (1996) depicts the onset of GVHD in individual mice of the different experimental groups. In 12/25 animals treated with Copolymer 1 the onset of GVDH was delayed with a range of 32–112 days after transplant (median of 73 days) as compared to control mice treated with either PBS (median onset of 21 days) or HEL (median onset 22 days). Nine of 25 animals treated with the observation period of 140 days after transplant (FIG. 3A of Schlegel et al., 1996). Furthermore, treatment with Copolymer 1 improved overall disease severity as gauged by the disease severity score (FIG. 3B of Schlegel et al., 1996) and by mean body weight curves of transplanted animals (FIG. 3D of Schlegel et al., 1996).

Similar results were obtained with Batch II of Copolymer 1.

(iii) Effect of Copolymer 1 treatment on survival. Treatment with Copolymer 1 (Batch I) improved long-term survival from lethal graft-versus-host disease. As shown in FIG. 3C of Schlegel et al. (1996), 14/25 (56%) of Copolymer 1-treated mice survived more than 140 days after transplant as compared to 2/26 of PBS treated or to 1/10 of HEL treated control mice (P<0.01). Treatment with HEL did not improve long-term survival.

Similar experiments were performed using Copolymer 1 Batch I (FIG. 2A of U.S. Pat. No. 5,858,964) or Batch II (FIG. 2B of U.S. Pat. No. 5,858,964). Thus, treatment with Copolymer 1 for the first nine weeks after bone marrow transplantation improved long-term survival from lethal GVHD.

(iv) Documentation of Engraftment. PCR analysis was performed 100 days after transplantation as described in Materials and Methods, to document long-term engraftment of allogeneic bone marrow cells. DNA polymorphism based on length variation in tandem repeat sequences of a microsatellite in the murine IL-1 gene was used as marker to differentiate between donor-derived (B10.D2/nSnJ) and recipient (BALB/c) peripheral blood mononuclear cells. Long-term engraftment of donor-derived cells, i.e., complete chimerism, was demonstrated in allogeneic mice by PCR analysis irrespective of the treatment received.

Example 5

Bone Marrow Transplantation in Mice, Induction of GVHD and Treatment with D-Copolymer 1

(i) Effect of D-Copolymer 1 Treatment on the Incidence, Onset and Severity of GVHD. Recipient mice were treated with 60 µg of D-Copolymer 1 or PBS daily for the first five weeks after transplant followed by a tapering schedule over an additional four weeks. The dosage of 60 µg/injection was selected based on the prolonged half-life of D-Copolymer 1 and was administered ip. Treatment was initiated on day −1 and after five weeks the frequency of injections was tapered to three times per week for the following two weeks and to two times per week for another two weeks. Once a week the D-Copolymer 1 was administered with incomplete Freund's adjuvant (IFA) ip as a depot dose. Treatment was discontinued after 9 weeks.

The results are shown in FIG. 3 of U.S. Pat. No. 8,858,964 and Table 3. D-Copolymer 1 treatment reduced the overall incidence of GVHD after allogeneic bone marrow transplantation from 100% (7/7) in control mice to 43% (3/7) in D-Copolymer 1-treated animals on day 30. Two of seven animals treated with D-Copolymer 1 did not develop any signs of GVHD beyond the observation period of 140 days after transplantation. Furthermore, treatment with D-Copolymer 1 improved overall disease severity as gauged by the mean disease score (Table 3).

TABLE 3

Effect of Treatment with D-Cop 1 on the Induction of GVHD in B10.D2 → BALB/c Recipients

| Group | n | Incid. day 30 | Incid. day 100 | Incid. day 140 | Mean Onset[1] (days) | Mean Severity[1] | MST (days) | % Actuarial Survival (day) |
|---|---|---|---|---|---|---|---|---|
| D-Cop 1 | 7 | 3/7 | 5/7 | 5/7 | 5/7 | 34.8 | >140 | 71.4 (140) |
| PBS | 7 | 7/7 | 7/7 | ↑↑ | ↑↑ | 21.9 | 60.5 | 0 (96) |

[1]Means are stated as overall means of the respective groups.
↑↑ GVHD-related mortality
MST: median survival time (in days)

(ii) Effect of D-Copolymer 1 Treatment on Survival. Treatment with D-Copolymer 1 improved long-term survival from lethal graft-versus-host disease. As shown in FIG. 3 of U.S. Pat. No. 5,858,964 and Table 3, 5/7 (71.4%) of experimental mice survived more than 140 days after transplant as compared to 0/7 of PBS-treated control mice.

Example 6

Prevention of GVHD in Humans (i) Patients. A protocol is established for patients aged 60 years or less and eligible for allogeneic bone marrow transplantation from histocompatible sibling donors for acute non-lymphoblastic leukemia or acute lymphoblastic leukemia not in first remission, chronic myelogenous leukemia not in chronic phase or relapsed patients with non-Hodgkin's lymphoma. Without bone marrow transplantation, these patients have expected survival measured in months. The benefits for these subjects is the use of high dose therapy in curing their disease and the potential prophylaxis against morbidity associated with allogeneic bone marrow transplantation, such as GVHD.

(ii) Conditioning Regimen. Patients are submitted to a conditioning regimen comprising fractionated total body irradiation by administering 120 cGy per fraction 2 to 3 times daily over 4 days (days −8 to −5) to a total dose of 1200 cGy, a multiple drug treatment including, e.g., etoposide (60 mg/kg) over 4 hours at day −4, cyclophosphamide (60 mg/kg) over 1 hour at day −2, antibacterial agents, and standard prophylaxis agents against GVHD, e.g., cyclosporine, FK506, methotrexate and prednisone.

(iii) GVHD Prophylaxis. Copolymer 1 is administered to the patient subcutaneously (sc), intramuscularly (im) or intravenously (iv) at a dosage of 1–500 mg twice daily. The treatment starts at day −2 before and is continued until day +60 after the allogeneic bone marrow transplantation (BMT). This day is chosen since nearly all of the acute GVHD that may occur, will do so by day +40.

Standard prophylaxis against GVHD with cyclosporine and prednisone is also continued. Cyclosporine is administered until the patient is able to sustain oral caloric intake and has no evidence of gastrointestinal toxicity (usually around the end of the first month, fourth week following BMT), at a dose from 1.5 to 5 mg/kg iv twice daily, by infusion in the first 35 days and then orally (per os) until the end of the treatment (day +180). Serum samples are obtained and, if necessary, the drug concentration is adjusted to prevent drug-related toxicities. The aim is for a level of cyclosporine between 200–500 ng/ml. Methylprednisolone is administered iv until patients can be switched to oral (p.o.) Prednisone. For example, it is administered iv at a dose of 0.25 mg/kg–0.5 mg/kg from day +7 to +28 and p.o. at a dose of 0.4 mg/kg–0.1 mg/kg until the end of the treatment (day +180).

The first phase of the treatment is to establish engraftment. If engraftment is established, the post-transplantation immunosuppression is then stepwise decreased. The first step is to stop the use of prednisone. If no GVHD occurs, then the use of cyclosporine is stopped (see statistical analysis). At that time only the random copolymer is used as the immunosuppressive regimen.

(iv) Statistical Analysis. Current engraftment success rate of bone marrow is close to 100% with a rate of about 50% at 20 days for patients satisfying the eligibility criteria of this protocol. Among these patients, the rate of relapse depends on the disease and remission status. The time to relapse curve is well approximated by an exponential curve over this interval. Both the engraftment rate at 20 days and the relapse rate are monitored statistically as the data become available on other patients treated by the same protocol.

The engraftment rate at 20 days provides the basis for stopping early to avoid putting more patients at risk than necessary if the stem cells take longer to engraft than anticipated. The binary endpoint of success by the twentieth day is monitored by sequential test, using 20 as the hypothesized median based on past experience, and using a boundary for inferiority fixed to provide a Type I risk of 5% (one sided) and a degree of conservatism midway between constant p level and the O'Brien-Fleming approach.

As the treatment proceeds, the data on relapse is also monitored, using the time to relapse as the endpoint and including all patients under treatment, whether engraftment is successful at the twentieth day or not.

Example 7

Effect of Copolymer 1 on Graft Rejection (HVGD) in the B10.D2→BALB/c Model

The feasibility of using Copolymer 1 for the prevention of graft rejection was first tested on transplantation systems across minor histocompatibility barriers. Thus, recipient mice (BALB/c) were transplanted with grafts from another strain (B10.D2), but of the same H-2 haplotype (H-$2^d$), such that donors and recipients differed only in minor histocompatibility antigens (transplantation across minor histocompatibility barriers). This model closely resembles the clinical setting in the majority of human transplantations, in which donor and recipient are usually HLA matched.

The effect of Copolymer 1 was compared to the effect of control PBS treatment in two transplantation systems:

(i) Skin graft transplantation which usually results in a vigorous rejection process more difficult to suppress than other organ rejection (Isakov et al., 1979); and (ii) Thyroid graft transplantation into the kidney's capsule which enables objective and quantitative indication not only of graft survival but also of the function (iodine uptake) of the transplanted thyroid tissue.

To test the effect of Copolymer 1 treatment on skin graft rejection in the B10.D2→BALB/c model, BALB/c recipient mice were transplanted with skin grafts from B10.D2 donors and treated daily with: PBS ip from day −7, Copolymer 1 (ip+sc) from day −7. Grafts were inspected daily. Rejection was considered positive when no viable donor epidermis remained. The results are summarized in Tables 4 and 6. The mean graft survival time (MST) in Copolymer 1-treated mice (600 µg/day) was 34 days in comparison to 26 days in PBS-treated mice (Table 6). In another experiment, treatment with 300 µg/day Copolymer 1 resulted in MST of 20.4 days and treatment with 600 µg/day resulted in 20.6 days, while the PBS control treatment resulted in MST of 16.1 days (Table 4). Thus Cop 1 induced significant beneficial effect on skin graft survival in the B10D2→BALB/c system.

To test the effect of Copolymer 1 treatment on the function of transplanted thyroids in the B10.D2→BALB/c model, thyroid glands from donors B10.D2 were transplanted in the kidney's capsules of BALB/c mice. After one week the transplanted mice were injected with $^{125}$I, and the radioactivity of each kidney was measured 20 hours later. cpm was calculated by subtracting the $^{125}$I absorbance of the untransplanted kidneys from the $^{125}$I absorbance of the recipient kidneys in the same treatment. The mean function index (MFI) for each treatment was calculated by dividing the mean $^{125}$I absorbance of (transplanted kidney-untransplanted kidney) in the tested treatment by the mean $^{125}$I absorbance of (transplanted kidney-untransplanted kidney) in the PBS treatment, as follows:

$$\text{MFI} \frac{\text{mean } \Delta \text{cpm for the Cop 1 tested treatment}}{\text{mean } \Delta \text{cpm for the PBS tested treatment}}$$

The results of thyroid transplantation are summarized in Tables 5 and 7. The MFI of the Copolymer 1-treated mice (600 µg/day) was 3.2 folds in one experiment and 5.2 folds in another experiment over PBS-treated mice. Thus Copolymer 1 treatment was significantly effective in preventing the functional deterioration of transplanted thyroid grafts in the B10D2→BALB/c system.

These results show that Copolymer 1 induced significant and prominent effect on graft survival and function in both skin graft and thyroid transplantation systems.

Additional studies were then conducted with mice in order to establish the ability of Cop 1 to inhibit graft rejection of graft by host, using the two transplantation model systems described above while addressing the following aspects: (i) the effect of Copolymer 1 on HVGD in different murine strain combinations; and (ii) the effect of Copolymer 1 on HVGD in comparison to the effect of other immunosuppressive drugs that are currently used for human transplantation, namely FK506 and cyclosporin A.

TABLE 4

Effect of Copolymer 1 Treatment on Skin Graft Rejection in the B10.02 → BALB/c Model

| Treatment | | N | MST* ± SD | P** |
|---|---|---|---|---|
| PBS | | 26 | 16.1 ± 2.2 | |
| Cop 1 | 300 µg/day | 10 | 20.4 ± 4.5 | <0.001 |
| Cop 1 | 600 µg/day | 34 | 20.6 ± 3.3 | <0.001 |
| Cy A | 1 µg/day | 10 | 17.8 ± 2.4 | >0.05 |
| FK506 | 300 µg/day | 19 | 21.2 ± 4.3 | <0.001 |

*Mean Survival Time
**P values were obtained by analysis of variance (ANOVA)

TABLE 5

Effect of Cop 1 Treatment on the Function of Transplanted Thyroids in the B10.D2 → BALB/c Model

| | | | Mean $^{125}$I Absorption | | | |
|---|---|---|---|---|---|---|
| Treatment | | N | Transplanted Kidney (cpm) | Untransplanted Kidney (cpm) | cpm | MFI* | P** |
| PBS | | 10 | 1193 | 421 | 772 | 1.0 | |
| Cop 1 | 600 µg | 10 | 2901 | 450 | 2451 | 3.2 | 0.0005 |
| Cy A | 1 µg | 4 | 864 | 312 | 552 | 0.7 | 0.23 |
| FK506 | 300 µg | 6 | 3117 | 693 | 2424 | 3.1 | 0.002 |

*The mean function index (MFI) for each treatment was calculated as follows:

$$\text{MFI} \frac{\text{mean } \Delta \text{cpm for the Cop 1 tested treatment}}{\text{mean } \Delta \text{cpm for the PBS tested treatment}}$$

**P values were obtained by t test.

Example 8

The Effect of Copolymer 1 on HVGD in Different Murine Strain Combinations

In order to find out whether the beneficial effect induced by Copolymer 1 on HVGD represents a general phenomenon, we tested the ability of Copolymer 1 to inhibit graft rejection in additional strain combinations. Three murine strain combinations: B10.D2→BALB/c in the H-2$^d$ haplotype, C57BL→C3HSW in the H-2$^b$ haplotype, and B10PL→PL/J in the H-2$^u$ haplotype, were tested across minor histocompatibility barriers.

After testing the model of recipient/donor mice of different strains, but of the same H-2 haplotype, we also tested rejection in mice transplanted with grafts from donors of another H-2 haplotype (transplantation across major histocompatibility barriers), a model of HLA unmatched transplantation in humans.

Across major histocompatibility barriers transplantation was tested in C57BL→BALB/c in the H-2$^b$→H-2$^d$ haplotype. All these strain combinations were tested with Copolymer 1 both using skin and thyroid transplantations as described in Example 7.

As shown in Tables 6 and 7, Copolymer 1 inhibited graft rejection in all strain combinations as demonstrated by the prolongation of the skin graft survival (Table 6) as well as by the elevation in the thyroid iodine absorbance (Table 7) in the Copolymer 1-treated mice in comparison to the PBS-treated mice. Copolymer 1 significantly inhibited even the rejection of grafts from donors of different H-2 haplotypes (Tables 4 and 6) which usually induce a more potent rejection course than the rejection of H-2 matched transplants. These results indicate that Copolymer 1 is effective in suppressing immune rejection of grafts from various origins in different strain combinations, and thus may be effective in other species as well.

TABLE 6

Effect of Copolymer 1 Treatment on Skin Graft Rejection in Various Haplotypes

| Haplotype | Treatment | N | MST* ± SD |
|---|---|---|---|
| B10D2 → BALB H-2$^d$ | PBS | 26 | 16.1 ± 2.2 |
| H-2$^d$ | Cop 1 | 34 | 20.6 ± 3.3 |
| H-2$^b$ | PBS | 9 | 16.2 ± 1.0 |
|  | Cop 1 | 9 | 17.7 ± 2.1 |
| B10PL → PL/J H-2$^u$ | PBS | 10 | 15.1 ± 3.5 |
|  | Cop 1 | 9 | 17.6 ± 5.1 |
| C57BL → C3HSW H-2$^b$ → H-2$^d$ | PBS | 18 | 14.0 ± 1.8 |
|  | Cop 1 | 18 | 18.5 ± 3.3 |

*Mean Survival Time.

Thyroid glands from B10.D2 donors were transplanted in the kidney's capsules of BALB/c mice. The results are shown in Tables 4 and 5. While CyA induced no significant beneficial effect in these systems, FK 506 significantly improved grafts survival/function in both the skin and the thyroid transplantation systems. Cop 1 also induced significant beneficial effect on graft survival/function similar to the effect of FK 506. While Cop 1 effect on skin graft survival was somewhat smaller than the effect of FK 506 (MST 20.6 for Cop 1 in comparison to 21.2 for FK 506 (Table 4), Cop 1 was as effective as FK 506, in preventing the functional deterioration of transplanted thyroid grafts (3.2 and 3.1 folds over the PBS control for Cop 1 and FK 506 respectively, Table 5).

Having now fully described this invention, it will be appreciated that by those skilled in the art that the same can be performed within a wide range of equivalent parameters, concentrations, and conditions without departing from the spirit and scope of the invention and without undue experimentation.

While this invention has been described in connection with specific embodiments thereof, it will be understood that it is capable of further modifications. This application is

TABLE 7

Effect of Cop 1 Treatment on Thyroid Rejection in Various Haplotypes

|  |  |  |  |  | Mean $^{125}$I Absorption | | |
|---|---|---|---|---|---|---|---|
|  | Treatment | N | Transplanted Kidney (cpm) | Untransplanted Kidney (cpm) | cpm | MFI* | P** |
| B10.D2 → BALB H-2$^d$ | PBS | 10 | 1193 | 421 | 772 | 1.0 |  |
|  | Cop 1 | 10 | 2901 | 450 | 2451 | 3.2 | 0.0005 |
| B10.D2 → BALB H-2$^d$ | PBS | 5 | 354 | 180 | 174 | 1.0 |  |
|  | Cop 1 | 5 | 1035 | 137 | 898 | 5.2 | 0.0014 |
| C57BL → C3H H-2$^b$ | PBS | 7 | 893 | 293 | 600 | 1.0 |  |
|  | Cop 1 | 4 | 1643 | 281 | 1362 | 2.3 | 0.0023 |
| B10PL → PL/J H-2$^d$ | PBS | 7 | 1201 | 518 | 683 | 1.0 |  |
|  | Cop 1 | 6 | 2009 | 332 | 1677 | 2.5 | 0.0016 |
| C57BL → BALB H-2$^b$ → H-2$^d$ | PBS | 8 | 4021 | 766 | 3255 | 1.0 |  |
|  | Cop 1 | 10 | 10759 | 924 | 9835 | 3.0 | 0.002 |

*The mean function index (MFI) for each treatment was calculated as follows:

$$MFI = \frac{\text{mean } \Delta\text{cpm for the Cop 1 tested treatment}}{\text{mean } \Delta\text{cpm for the PBS tested treatment}}$$

**P values were obtained by t test.

Example 9

The Effect of Cop 1 treatment on HVGD in Comparison to Other Immunosuppressive Drugs The effect of Cop 1 in comparison to the effect of two other immunosuppressive drugs that are currently used to prevent graft rejection in human transplantation, FK506 and cyclosporin A (CyA), was tested in the two model systems.

BALB/c recipient mice were transplanted with skin grafts originated in B10.D2 donors and treated daily with: PBS ip from day −7, Cop 1 (ip+sc) from day −7, CyA ip from day −7, and FK 506 ip 7 injections from day −2 before transplantation. Grafts were inspected daily. Rejection was considered positive when no viable donor epidermis remained.

intended to cover any variations, uses, or adaptations of the inventions following, in general, the principles of the invention and including such departures from the present disclosure as come within known or customary practice within the art to which the invention pertains and as may be applied to the essential features hereinbefore se forth as follows in the scope of the appended claims.

All references cited herein, including journal articles or abstracts, published or unpublished U.S. or foreign patent applications, issued U.S. or foreign patents or any other references, are entirely incorporated by reference herein, including all data, tables, figures, and text presented in the cited references. Additionally, the entire contents of the references cited within the reference cited herein are also entirely incorporated by reference.

Reference to known method steps, conventional method steps, known methods or conventional methods is not any way an admission that any aspect, description or embodiment of the present invention is disclosed, taught or suggested in the relevant art.

The foregoing description of the specific embodiments will so fully reveal the general nature of the invention that others can, by applying knowledge within the skill of the art (including the contents of the references cited herein), readily modify and/or adapt for various applications such specific embodiments, without undue experimentation, without departing from the general concept of the present invention. Therefore, such adaptations and modifications are intended to be within the meaning and rang of equivalents of the disclosed embodiments, based on the teaching and guidance presented herein. It is to be understood that the phraseology or terminology herein is for the purpose of description and not of limitation, such that the terminology or phraseology of the present specification is to be interpreted by the skilled artisan in light of the teachings and guidance presented herein, in combination with the knowledge of one of ordinary skill in the art.

REFERENCES

Aharoni et al., "T suppressor hybridomas and interleukin-2-dependent lines induced by copolymer 1 or by spinal cord homogenate down-regulate experimental allergic encephalomyelitis", *Eur. J. Immunol.* 23:17–25 (1993).

Aharoni et al., "Studies on the mechanism and specificity of the effect of the synthetic random copolymer GLAT on graft-versus-host disease", *Immunology Letters*, 58(2): 79–87 (1997).

Bornstein et al., "Clinical trials of Cop 1 in multiple sclerosis", *Handbook of Multiple Sclerosis*, ed. Cook S. D. Marcel Dekker, Inc., p. 469 (1990).

Fridkis-Hareli et al., "Direct binding of myelin basic protein and synthetic copolymer 1 to class II major histocompatibility complex molecules on living antigen-presenting cells—specificity and promiscuity", *Proc. Natl. Acad. Sci. USA* 91:4872–76 (1994).

Isakov et al., "Differential immunogenic expression of an H-2-linked histocompatibility antigen on different tissues. Differences in survival between heart, thyroid, and skin allografts", *Transplantation*, 28(1):31–5 (1979).

Ishioka et al., "Failure to demonstrate long-lived MHC saturation both in vitro and in vivo. Implications for therapeutic potential of MHC-blocking peptides", *J. Immunol.* 152(9):4310–4319 (1994).

Jacob et al., "DNA polymorphism in cytokine genes based on length variations in simple-sequence tandem repeats" *Immunogenetics*, 38:251 (1993).

Johnson et al., "Cop 1 positive results—a phase III trial in relapsing remitting", MS. 11th Annual Meeting A.N.A. (1994).

Johnson et al., "Copolymer 1 reduces relapse rate and improves disability in relapsing-remitting multiple sclerosis: results of a phase III multicenter, double-blind placebo-controlled trial. The Copolymer 1 Multiple Sclerosis Study Group." *Neurology*, 1:65 (1995).

Schlegel et al., "Prevention of graft-Versus-host Disease by Peptides Binding to Class II Major Histocompatibility Complex Molecules" *Blood* 84:2802–10 (1994).

Schlegel et al., "A synthetic random basic copolymer with promiscuous binding to class II major histocompatibility complex molecules inhibits T-cell proliferative responses to major and minor histocompatibility antigens in vitro and confers the capacity to prevent murine graft-versus-host disease in vivo", *Proc. Natl. Acad. Sci. USA*, 93:5061–6 (1996).

Sela et al., *Bull. Inst. Pasteur (Paris)* 88:303–314 (1990).

Sykes et al, "Immunobiology of transplantation", *FASEB J*, 10(7):721–30 (1996).

Teitelbaum et al., "Suppression of experimental allergic encephalomyelitis by a synthetic polypeptide" *Eur. J. Immunol.* 1:242–48 (1971).

Teitelbaum et al., "Suppression by several synthetic polypeptides of experimental allergic encephalomyelitis induced in guinea pigs and rabbits with bovine and human basic encephalitogen", *Eur. J. Immunol.* 3:272 (1973).

Teitelbaum et al., "Suppression of experimental allergic encephalomyelitis in rhesus monkeys by a synthetic basic copolymer", *Clin. Immunol. Immunopathol.* 3:256 (1974a).

Teitelbaum et al., "Suppression of experimental allergic encephalomyelitis in baboons by Cop 1", *Israel J. Med. Sci.* 13:1038 (1974b).

Teitelbaum et al., "Specific inhibition of the T-cell response to myelin basic protein by the synthetic copolymer Cop 1", *Proc. Natl. Acad. Sci USA* 85:9724–28 (1988).

Webb et al., "Molecular requirements involved in suppression of EAE by synthetic basic copolymers of amino acids", *Immunochemistry* 13:333–337 (1976).

Webb et al., "Extrathymic tolerance of mature T cells: clonal elimination as a consequence of immunity", *Cell*, 63:1249–1256 (1990).

The invention claimed is:

1. A method for treating or suppressing host-versus-graft disease (HVGD) in a mammalian transplant recipient, comprising administering a therapeutically effective amount of an active ingredient that is a random copolymer consisting of amino acid residues selected from the group consisting of one amino acid from at least three of the following groups, the groups consisting of:
   (a) lysine and arginine;
   (b) glutamic acid and aspartic acid;
   (c) alanine and glycine;
   (d) tyrosine and tryptophan.

2. The method according to claim 1, wherein the copolymer consists of four different amino acids each from one of the groups (a) to (d).

3. The method according to claim 2, wherein the copolymer consists of a combination of alanine, glutamic acid, lysine, and tyrosine, of net overall positive electrical charge and of a molecular weight of 2,000 to 40,000 daltons.

4. The method according to claim 3 wherein the copolymer has a molecular weight of 2,000 to 13,000 daltons.

5. The method according to claim 4, wherein the copolymer is Copolymer 1 of average molecular weight of 4,700 to 13,000 daltons.

6. The method according to claim 1, wherein the copolymer consists of three different amino acids each from one of three groups of the groups (a) to (d), herein referred to as a terpolymer.

7. The method according to claim 6, wherein the random terpolymer consists of the amino acids tyrosine, alanine and lysine.

8. The method according to claim 7, wherein the terpolymer consists of tyrosine, alanine and lysine, in the molar ratio of from 0.005 to 0.25 tyrosine, from 0.3 to 0.6 alanine, and from 0.1 to 0.5 lysine, herein designated YAK.

9. The method according to claim 6, wherein the random terpolymer consists of the amino acids glutamic acid, tyrosine, and lysine.

10. The method according to claim 9, wherein the random terpolymer consists of the amino acids glutamic acid, tyrosine, and lysine in the molar ratio of from 0.005 to 0.300 glutamic acid, from 0.005 to 0.250 tyrosine, and from 0.3 to 0.7 lysine, herein designated YEK.

11. The method according to claim 6, wherein the random terpolymer consists of the amino acids tyrosine, glutamic acid, and alanine.

12. The method according to claim 11, wherein the random terpolymer consists of the amino acids tyrosine, glutamic acid, and alanine in the molar ratio of from 0.005 to 0.25 tyrosine, from 0.005 to 0.3 glutamic acid, and from 0.005 to 0.8 alanine, herein designated YEA.

13. The method according to claim 6, wherein the random terpolymer consists of the amino acids glutamic acid, alanine and lysine.

14. The method according to claim 13, wherein the random terpolymer consists of the amino acids glutamic acid, alanine and lysine in the molar ratio of from 005 to 0.3 glutamic acid, from 0.005 to 0.6 alanine, and from 0.2 to 0.7 lysine, herein designated KEA.

15. The method according to any one of claims 1 to 14, wherein the amino acids in the copolymers are all L-, all D- or a mixture of L- and D-amino acids.

16. The method according to claim 1, wherein said patient receives an HLA matched or unmatched transplant.

17. The method according to claim 16, wherein said organ or tissue is any one of heart, lung, kidney, liver, bone marrow or skin.

18. The method according to claim 1, wherein the copolymer is Copolymer 1 of average molecular weight of 2,000 to 20,000 daltons.

* * * * *

UNITED STATES PATENT AND TRADEMARK OFFICE
CERTIFICATE OF CORRECTION

| | | |
|---|---|---|
| PATENT NO. | : 7,053,043 B1 | Page 1 of 1 |
| APPLICATION NO. | : 09/831629 | |
| DATED | : May 30, 2006 | |
| INVENTOR(S) | : Aharoni et al. | |

It is certified that error appears in the above-identified patent and that said Letters Patent is hereby corrected as shown below:

On The Title Page Item (75), in the list of inventors insert --Michael Sela (IL) --.

On The Title Page Item (60), insert --Provisional-- application No. 60/108,184, filed on Nov. 12, 1998.--

3) Column 1, line 14, after "1999" insert --and 60/108,184 filed on Nov. 12, 1998--.

Signed and Sealed this

Twentieth Day of November, 2007

JON W. DUDAS
*Director of the United States Patent and Trademark Office*